United States Patent
Cole

(10) Patent No.: US 10,646,684 B2
(45) Date of Patent: May 12, 2020

(54) REVERSIBLE COMPONENT FOR MULTIPLE RESPIRATORY SUPPORT MODES

(71) Applicant: KONINKLIJKE PHILIPS N.V., Eindhoven (NL)

(72) Inventor: Kenneth E. Cole, New Alexandria, PA (US)

(73) Assignee: Koninklijke Philips N.V., Eindhoven (NL)

( * ) Notice: Subject to any disclaimer, the term of this patent is extended or adjusted under 35 U.S.C. 154(b) by 585 days.

(21) Appl. No.: 15/103,914

(22) PCT Filed: Dec. 8, 2014

(86) PCT No.: PCT/IB2014/066685
§ 371 (c)(1),
(2) Date: Jun. 13, 2016

(87) PCT Pub. No.: WO2015/092605
PCT Pub. Date: Jun. 25, 2015

(65) Prior Publication Data
US 2016/0317780 A1     Nov. 3, 2016

Related U.S. Application Data

(60) Provisional application No. 61/917,029, filed on Dec. 17, 2013.

(51) Int. Cl.
*A61M 16/20*     (2006.01)
*A61M 16/08*     (2006.01)
(Continued)

(52) U.S. Cl.
CPC ...... *A61M 16/208* (2013.01); *A61M 16/0057* (2013.01); *A61M 16/0465* (2013.01);
(Continued)

(58) Field of Classification Search
CPC .............. A61M 16/00; A61M 16/0003; A61M 16/0051; A61M 16/0057–0072;
(Continued)

(56) References Cited

U.S. PATENT DOCUMENTS

| 5,239,994 A | 8/1993 | Atkins |
| 6,739,334 B2 | 5/2004 | Valeij |

(Continued)

FOREIGN PATENT DOCUMENTS

| EP | 0283141 A2 | 9/1988 |
| EP | 0512285 A1 | 11/1992 |

(Continued)

*Primary Examiner* — Rachel T Sippel
(74) *Attorney, Agent, or Firm* — Daniel H. Brean

(57) ABSTRACT

Systems and methods for coupling a respiratory support circuit (5, 5a) to a pressure generator (140) include multiple flow paths 13,17) for corresponding modes of operation. A first flow path (13) for a first mode of operation couples fluidly between the pressure generator, through a control port (12) and a circuit port (14), to an exhalation limb (20) of a dual-limb configuration of a respiratory support circuit. A second flow path (17) for a second mode of operates couples fluidly between the pressure generator, through a control port (16) and a circuit port (18), an exhalation valve (21) of a single-limb configuration of the respiratory support circuit.

15 Claims, 3 Drawing Sheets

(51) Int. Cl.
    *A61M 16/00*       (2006.01)
    *A61M 16/04*       (2006.01)
    *A61M 16/06*       (2006.01)

(52) U.S. Cl.
    CPC ........ *A61M 16/06* (2013.01); *A61M 16/0816* (2013.01); *A61M 16/0875* (2013.01); *A61M 16/0883* (2014.02); *A61M 16/206* (2014.02); *A61M 2205/50* (2013.01)

(58) Field of Classification Search
    CPC .............. A61M 16/08; A61M 16/0916; A61M 16/0875–0891; A61M 16/20–209
    See application file for complete search history.

(56) References Cited

U.S. PATENT DOCUMENTS

| | | |
|---|---|---|
| 2005/0005937 A1 | 1/2005 | Farrugia |
| 2007/0144516 A1 | 6/2007 | Doyle |
| 2011/0197883 A1 | 8/2011 | McDaniel |
| 2011/0197884 A1 | 8/2011 | Duff |
| 2011/0259332 A1 | 10/2011 | Sancez |
| 2013/0006133 A1 | 1/2013 | Doyle |

FOREIGN PATENT DOCUMENTS

| | | |
|---|---|---|
| JP | 1501365 A | 5/1989 |
| JP | 2000342691 A | 12/2000 |
| WO | WO2009117422 A2 | 9/2009 |
| WO | WO2013037759 A1 | 3/2013 |

REVERSIBLE COMPONENT FOR MULTIPLE RESPIRATORY SUPPORT MODES

CROSS-REFERENCE TO RELATED APPLICATIONS

This patent application claims the priority benefit under 35 U.S.C. § 371 of international patent application no. PCT/IB2014/066685, filed Dec. 8, 2014, which claims the priority benefit under 35 U.S.C. § 119(e) of U.S. Provisional Application No. 61/917,029 filed on Dec. 17, 2013, the contents of which are herein incorporated by reference.

BACKGROUND

1. Field

The present disclosure pertains to systems and methods for coupling a respiratory support circuit to a pressure generator, and, in particular, to systems and methods that provide coupling in multiple modes of operation of the respiratory support circuit.

2. Description of the Related Art

It is common to treat patients with respiratory therapy. Some examples of respiratory therapy use a respiratory support circuit. Different types of respiratory support circuits may be used for different types of respiratory therapy. Respiratory support circuits may include one or more of a single-limb configuration, a dual-limb configuration, and/or other configurations.

SUMMARY

Accordingly, it is an object of one or more embodiments of the present invention to provide an apparatus. The apparatus includes a body configured to be coupled operatively with a pressure generator and tubing to provide a respiratory support circuit to a subject. The body is configured to effectuate switching between a first mode of operation and a second mode of operation. The body includes a first and second control port, a first and second circuit port, and a first and second flow path. The first control port is configured to couple fluidly with the pressure generator. The first circuit port is configured to couple fluidly with an exhalation limb of the respiratory support circuit. The first flow path is formed between the first control port and the first circuit port. The first flow path is used in the first mode of operation. The second control port is configured to couple fluidly with the pressure generator. The second circuit port is configured to couple fluidly with an exhalation valve of the respiratory support circuit. The second flow path is formed between the second control port and the second circuit port. The second flow path is used in the second mode of operation.

It is yet another aspect of one or more embodiments of the present invention to provide a method of coupling a respiratory support circuit to a pressure generator. The method includes providing a body that includes a first and second control port and a first and second circuit port, wherein the body operates in either a first mode or a second mode of operation; coupling fluidly, by the first control port, with the pressure generator; coupling fluidly, by the first circuit port, with an exhalation limb of the respiratory support circuit; forming a first flow path between the first control port and the first circuit port, wherein the first flow path is used in the first mode of operation; coupling fluidly, by the second control port, with the pressure generator; coupling fluidly, by the second circuit port, with an exhalation valve of the respiratory support circuit; and forming a second flow path between the second control port and the second circuit port, wherein the second flow path is used in the second mode of operation.

It is yet another aspect of one or more embodiments to provide a system configured to couple a respiratory support circuit to a pressure generator. The system includes means for providing a first and second control port and a first and second circuit port, the means configured to effectuate switching between a first mode and a second mode of operation; first means for coupling fluidly with the pressure generator; means for coupling fluidly with an exhalation limb of the respiratory support circuit; means for forming a first flow path between the first control port and the first circuit port, the means for forming the first flow path being used in the first mode of operation; second means for coupling fluidly with the pressure generator; means for coupling fluidly with an exhalation valve of the respiratory support circuit; and means for forming a second flow path between the second control port and the second circuit port, the means for forming the second flow path being used in the second mode of operation.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
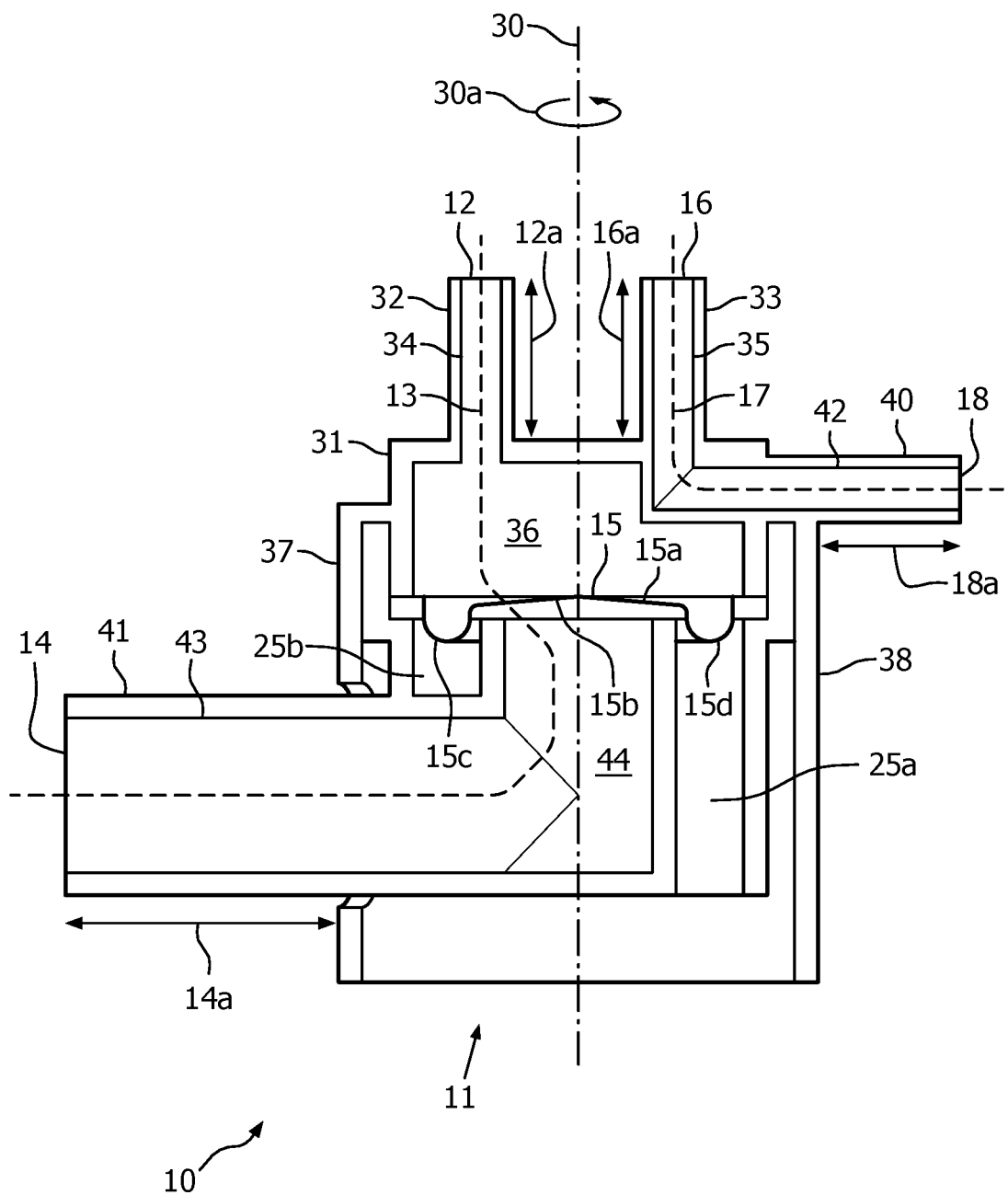
FIG. 1 illustrates a schematic view of an apparatus in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2A:
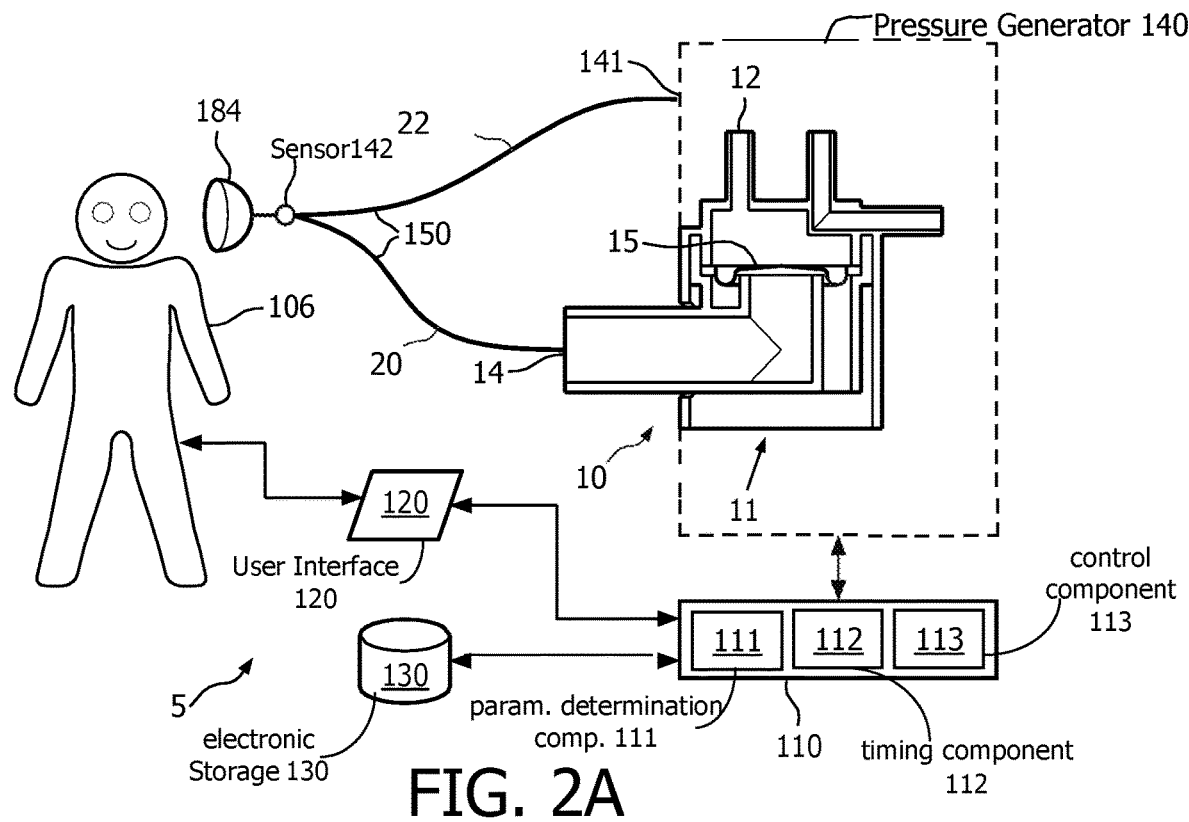
FIGS. 2A-2B illustrate views of an apparatus used to couple a respiratory support circuit to a pressure generator in accordance with one or more embodiments.
Figure 2B:
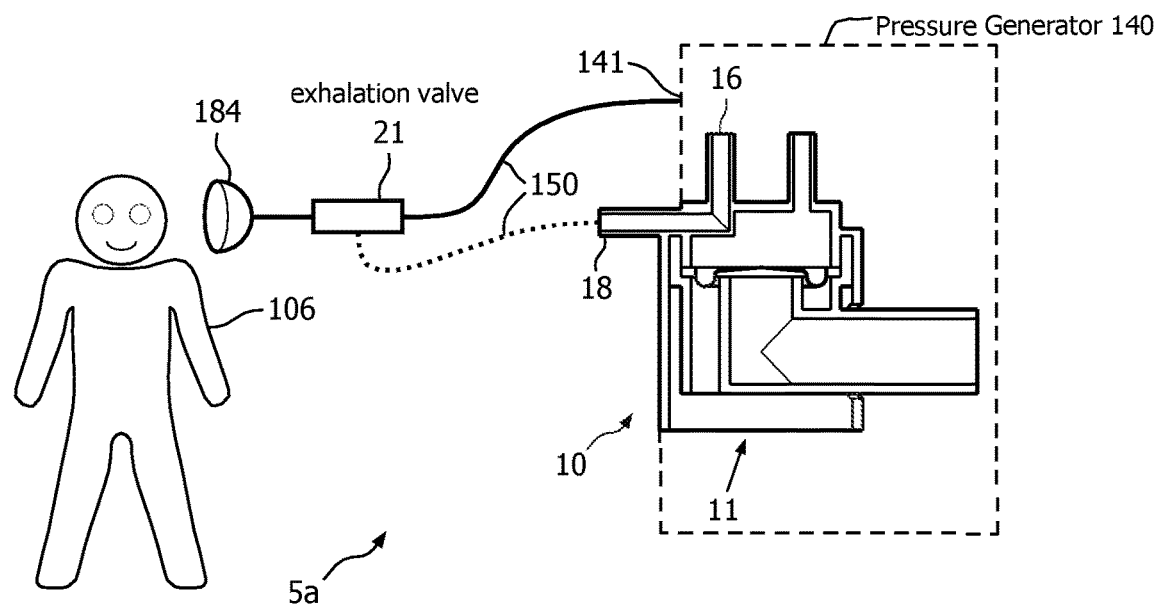

FIG. 1 illustrates an apparatus 10 for coupling a respiratory support circuit (not shown in FIG. 1) to a pressure generator (not shown in FIG. 1). The respiratory support circuit may be used to provide respiratory therapy to a patient. As illustrated in FIGS. 2A and 2B, a patient may interchangeably be referred to as a subject 106. Apparatus 10 can be integrated, embedded, incorporated, combined, and/or otherwise operating in conjunction with a pressure generator, including but not limited to a pressure generator 140 shown in FIGS. 2A and 2B. Apparatus 10 includes one or more of a body 11, a central portion 31, a first control port 12, a second control port 16, a first circuit port 14, a second circuit port 18, and/or other components. Body 11 is configured to be coupled operatively with a pressure generator and/or tubing to provide a respiratory support circuit. Body 11 may be configured to effectuate switching between different modes of operation, as described elsewhere herein. Apparatus 10 may have an axis of symmetry 30, around which apparatus 10 may be rotated in a direction 30a, for example by 180 degrees, e.g. to support switching between different modes of operation. First control port 12 and second control port 16 may be positioned at equal or similar distances from axis of symmetry 30, e.g. on opposite sides thereof.

Referring to FIGS. 1, 2A, and 2B, in some embodiments, apparatus 10 and/or body 11 may include one or more of a first flow path 13, a second flow path 17, a valve 15, a first outer surface 37, a second outer surface 38, a processor 110, a user interface 120, electronic storage 130, a parameter determination component 111, a timing component 112, a control component 113, and/or other components. First control port 12 is configured to couple fluidly with pressure generator 140. First control port 12 may be configured to couple with a control port interface (not shown) of pressure generator 140. First control port 12 may protrude from central portion 31 by a first control port length 12a. First control port 12 may include an outer surface 32, an inner surface 34, and/or other surfaces and/or components. Outer surface 32 may be coupled and/or connected to central portion 31. Inner surface 34 may form part of first flow path 13.

In some embodiments, first circuit port 14 may be configured to couple fluidly with an exhalation limb 20 of a respiratory support circuit. In some embodiments, first circuit port 14 may be configured to form part of a respiratory support circuit, for example as depicted in FIG. 2A and described elsewhere herein. First flow path 13 may be formed between and/or including first control port 12 and first circuit port 14. In some embodiments, first flow path 13 may be used in a first mode of operation. In some embodiments, first outer surface 37 may be outward facing and/or visible during use of apparatus 10 in the first mode of operation, whereas second outer surface 38 may be inward facing and/or not visible during use of apparatus 10 in the first mode of operation. First circuit port 14 may protrude from central portion 31 by a first circuit port length 14a. As depicted in FIG. 1, first circuit port 14 may protrude in a different direction than first control port 12 and second control port 16. First circuit port 14 may include an outer surface 41, an inner surface 43, and/or other surfaces and/or components. Outer surface 41 may be coupled and/or connected to central portion 31. Inner surface 43 may form part of first flow path 13.

Second control port 16 is configured to couple fluidly with pressure generator 140. Second control port 16 may be configured to couple with a control port interface (not shown) of pressure generator 140. For example, second control port 16 may be configured to couple fluidly with the same control port interface as first control port 12, albeit in different modes of operation (e.g. not simultaneously, but rather during different periods, different treatment sessions, and/or different respiratory therapies). Second control port 16 may protrude from central portion 31 by a second control port length 16a. First control port length 12a may be the same as or similar to second control port length 16a. As depicted in FIG. 1, first control port 12 may protrude in the same or a similar direction as second control port 16. Second control port 16 may include an outer surface 33, an inner surface 35, and/or other surfaces and/or components. Outer surface 33 may be coupled and/or connected to central portion 31. Inner surface 35 may form part of second flow path 17.

In some embodiments, second circuit port 18 may be configured to couple fluidly with an exhalation valve 21 of a respiratory support circuit. In some embodiments, second circuit port 18 may be configured to form part of a respiratory support circuit, for example as depicted in FIG. 2B and described elsewhere herein. Second circuit port 18 may protrude from central portion 31 by a second circuit port length 18a. As depicted in FIG. 1, first circuit port 14 may protrude in the opposite direction as second circuit port 18. Second flow path 17 may be formed between and/or including second control port 16 and second circuit port 18. Second circuit port 18 may include an outer surface 40, an inner surface 42, and/or other surfaces and/or components. Outer surface 40 may be coupled and/or connected to central portion 31. Inner surface 42 may form part of second flow path 17.

In some embodiments, second flow path 17 may be used in a second mode of operation. In some embodiments, second outer surface 38 may be outward facing and/or visible during use of apparatus 10 in the second mode of operation, whereas first outer surface 37 may be inward facing and/or not visible during use of apparatus 10 in the second mode of operation.

In some embodiments, the first and second mode of operation may be mutually exclusive such that only one of the first and second modes of operation is active at any time. In some embodiments, body 11 may be configured to effectuate switching between modes of operation by virtue of the symmetry of body 11 (e.g. around axis of symmetry 30). For example, body 11 may be configured to couple with pressure generator 140 in multiple relative arrangements such that a first relative arrangement corresponds to the first mode of operation and the second relative arrangement corresponds to the second mode of operation. In some embodiments, switching between modes of operation may be accomplished by reversing (e.g. by 180 degree) the arrangement or position of body 11 relative to pressure generator 140. For example, note that the relative arrangement of body 11 in FIG. 2A is reversed in comparison to FIG. 2B.

Body 11 may include valve 15 arranged within and/or disposed along first flow path 13. The area above valve 15, within central portion 31, may form a chamber 36. Chamber 36 may be fluidly coupled to first control port 12. The area below valve 15, at least partially within central portion 31, may form a chamber 44. Chamber 44 may be fluidly coupled to first circuit port 14. Valve 15 may be configured to selectively exhaust gas through one or both of a body exhaust portion 25a and/or a body exhaust portion 25b. Body exhaust portions 25a and 25b may form chambers that couple fluidly with atmosphere and/or the area outside of apparatus 10. As depicted in FIG. 1, body exhaust portions 25a and 25b may be separate and distinct from chamber 36 and chamber 44. In some embodiments, fluid coupling between chamber 44 and body exhaust portions 25a and 25b is prevented by valve 15 when valve 15 is closed.

In some embodiments, valve 15 may include a rolling diaphragm valve. In some embodiments, valve 15 may include an upper valve surface 15a and a lower valve surface 15b as depicted in FIG. 1. Upper valve surface 15a may be disposed on the opposite side of lower valve surface 15b, as depicted. Upper valve surface 15a may form part of chamber 36. Lower valve surface 15b may form part of chamber 44. Responsive to the pressure at and/or near lower valve surface 15b exceeding the pressure at and/or near upper valve surface 15a and/or within chamber 36 (by an amount sufficient to exceed inherent inertia of valve 15 to movement and/or opening), valve 15 may open. In some embodiments, valve 15 includes valve exhaust portion 15c and valve exhaust portion 15d, arranged in operative engagement with body exhaust portion 25b and body exhaust portion 25a, respectively. Responsive to valve 15 opening, gas entering body 11 through first circuit port 14 may be exhausted (e.g. to atmosphere) from chamber 44 either through valve 15, valve exhaust portion 15c, and body exhaust portion 25b, and/or through valve 15, valve exhaust portion 15d, and body exhaust portion 25a.

In some embodiments, upper valve surface 15a (or at least its active area during operation) may be larger than lower valve surface 15b (or at least its active area during operation), such that valve 15 is biased to being closed. In some embodiments, if the pressure on either side of valve 15 (e.g. the upper side and the lower side) is equal, valve 15 may be configured to be closed. Alternatively, and/or simultaneously, in some embodiments, if the pressure in chamber 36 and chamber 44 is equal, valve 15 may be configured to be closed. During operation, pressure supplied through first control port 12 may be controlled and/or adjusted in order to open and/or close valve 15 during one or more particular (e.g. predetermined) portions of the respiratory cycle, as described in more details elsewhere herein.

Referring to FIGS. 2A and 2B, pressure generator 140 may be integrated, combined, or connected with a ventilator and/or (positive) airway pressure device (PAP/CPAP/Bi-PAP®/etc.) and configured to provide a pressurized flow of breathable gas for delivery to the airway of subject 106, e.g. via tubing 150. Tubing 150 may be referred to as delivery circuit 150 and/or subject interface 150. For example, system 5 of FIG. 2A includes apparatus 10, pressure generator 140, and/or other components. System 5 represents a particular respiratory support circuit in a particular configuration, configured to provide respiratory therapy. For example, system 5a of FIG. 2B includes apparatus 10, pressure generator 140, and/or other components. System 5a in FIG. 2B represents a particular respiratory support circuit in a different configuration than the depiction of FIG. 2A. Components and/or features depicted in any of FIGS. 1, 2A, and 2B are envisioned to be (potentially) included in embodiments of body 11, system 5, system 5a, and/or the respiratory support circuits of FIGS. 2A and 2B. For example, valve 15 in FIG. 2B may include an upper valve surface 15a as depicted in FIG. 1. For example, system 5b may include a user interface 120 as depicted in FIG. 2A, and so on and so forth.

Referring to FIGS. 2A and 2B, pressure generator 140 may be configured to adjust pressure levels, flow, humidity, velocity, acceleration, and/or other parameters of the pressurized flow of breathable gas in substantial synchronization with the breathing cycle of subject 106. Subject 106 may or may not initiate one or more phases of respiration. Respiratory therapy may be implemented as pressure control, pressure support, and/or volume control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Other schemes for providing respiratory therapy through the delivery of the pressurized flow of breathable gas are contemplated.

A pressurized flow of breathable gas may be delivered from pressure generator 140 to the airway of subject 106 via tubing 150. Tubing 150 may include a conduit (e.g. a flexible length of hose) and/or a subject interface appliance 184. FIGS. 2A and 2B illustrate dual-limb and single-limb configurations, respectively, of respiratory support circuits that place subject interface appliance 184 in fluid communication with pressure generator 140. Tubing 150 forms one or more flow paths through which the pressurized flow of breathable gas is communicated between subject interface appliance 184, pressure generator 140, and/or apparatus 10.

Subject interface appliance 184 in FIGS. 2A and 2B may be configured to deliver the pressurized flow of breathable gas to the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Apparatus 10 may be configured to operate in multiple modes of operation. By way of non-limiting example, the multiple modes of operation may include the first and second mode of operation, as described elsewhere herein. In some embodiments, different modes of operation may correspond to different types of respiratory therapy. Additional modes of operation and corresponding types of respiratory therapy are envisioned within the scope of this disclosure.

The first mode of operation may correspond to respiratory therapy using a dual-limb configuration of the respiratory support circuit. For example, in a dual-limb configuration, the respiratory support circuit may include an exhalation limb that is separate from an inhalation limb. FIG. 2A illustrates an example, in which exhalation limb 20 is coupled with first circuit port 14 and coupled with a subject interface appliance 184. In the dual-limb configuration depicted in FIG. 2A, an inhalation limb 22 is coupled with subject interface appliance 184 and with a circuit port 141 of a pressure generator 140. In some embodiments, circuit port 141 of pressure generator 140 may include an inhalation valve that may be a controllable and/or adjustable valve.

The second mode of operation may correspond to respiratory therapy using proximal airway pressure and/or positive airway pressure in a single-limb configuration of the respiratory support circuit. For example, in a single-limb configuration, the respiratory support circuit may include an exhalation valve in the flow path between the pressure generator and the subject. FIG. 2B illustrates an example, in which exhalation valve 21 is coupled fluidly with second circuit port 18. Pressure generator 140 may be configured to adjust and/or control exhalation valve 21 through second control port 16, second flow path 17, and/or second circuit port 18.

In some embodiments, apparatus 10 and/or a respiratory support circuit (as represented by system 5 in FIG. 2A for example) may include one or more sensors configured to generate output signals conveying information related to parameters of respiration, respiratory airflow, airway mechanics, physiology of subject 106, medical parameters, environmental parameters, and/or other parameters. FIG. 2A illustrates system 5 that includes a sensor 142 configured to generate output signals conveying information. By way of non-limiting example, parameters may include one or more of flow, (airway) pressure, humidity, velocity, acceleration, and/or other parameters. Sensor 142 may be in fluid communication with pressure generator 140, apparatus 10, and/or subject interface appliance 184. The number of sensors or the placement of sensors is not limited by the depiction in FIG. 2A.

Sensor 142 may generate output signals related to physiological parameters pertaining to subject 106. In some embodiments, one or more sensors may include one or more $CO_2$ sensors. Generated output signals may convey information related to parameters associated with the state and/or condition of an airway of subject 106, the breathing of subject 106, the gas breathed by subject 106, the composition of the gas breathed by subject 106, one or more $CO_2$ parameters of the gas breathed by subject 106, the delivery of the gas to the airway of subject 106, and/or a respiratory effort by the subject. The one or more $CO_2$ parameters and/or measurements may include, without limitation, end-tidal $CO_2$ measurements, volumetric $CO_2$ measurements, mixed-venous $CO_2$ measurements, arterial $CO_2$ measurements, and/or other $CO_2$ parameters and/or measurements. For example, a parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the previously listed parameters through a previously known and/or calibrated mathematical relationship. Resulting signals or information from the sensors may be transmitted to pressure generator 140, processor 110, user interface 120, electronic storage 130, and/or other components shown in FIGS. 1, 2A and/or 2B. This transmission may be wired and/or wireless.

The illustration of sensor 142 including one member in FIG. 2A is not intended to be limiting.

User interface 120 of system 5 in FIG. 2A is configured to provide an interface for subject 106 (or another user) through which the user can provide information to and/or receive information from system 5. This enables data, results, and/or instructions and any other communicable items, collectively referred to as "information," to be communicated between the user and system 5. An example of information that can be conveyed to subject 106 is the current mode of operation or operational setting of apparatus 10 and/or pressure generator 140. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided by user interface 120 in the form of auditory signals, visual signals, tactile signals, and/or other sensory signals, or any combination thereof.

By way of non-limiting example, user interface 120 may include a radiation source capable of emitting light. The radiation source includes, for example, one or more of at least one LED, at least one light bulb, a display screen, and/or other sources. User interface 120 may control the radiation source to emit light in a manner that conveys information to subject 106.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into system 5 from removable storage (e.g., a smart card, a flash drive, a removable disk, etc.) that enables the user(s) to customize the implementation of system 5. Other exemplary input devices and techniques adapted for use with system 5 as user interface 120 include, but are not limited to, an RS-232 port, RF link, an IR link, modem (telephone, cable, Ethernet, internet or other). In short, any technique for communicating information with system 5 is contemplated as user interface 120.

Electronic storage 130 of system 5 in FIG. 2A comprises electronic storage media that electronically stores information. The electronic storage media of electronic storage 130 may include one or both of system storage that is provided integrally (i.e., substantially non-removable) with system 5 and/or removable storage that is removably connectable to system 5 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 5 to function properly. For example, electronic storage 130 may record or store information related to the provided respiratory therapy, and/or other information. Electronic storage 130 may be a separate component within system 5, or is provided integrally with one or more other components of system 5 (e.g., processor 110).

Processor 110 of system 5 in FIG. 2A is configured to provide information processing and control capabilities in system 5. As such, processor 110 includes one or more of a digital processor, a microcontroller, an analog processor, a digital circuit designed to process information, an analog circuit designed to process information, a state machine, and/or other mechanisms for electronically processing information. Although processor 110 is shown in FIG. 2A as a single entity, this is for illustrative purposes only. In some implementations, processor 110 includes a plurality of processing units.

As is shown in FIG. 2A, processor 110 is configured to execute one or more computer program components. The one or more computer program components include one or more of parameter determination component 111, timing component 112, control component 113, and/or other components. Processor 110 is configured to execute components 111, 112 and/or 113 by software; hardware; firmware; some combination of software, hardware, and/or firmware; and/or other mechanisms for configuring processing capabilities on processor 110.

It should be appreciated that although components 111-113 are illustrated in FIG. 2A as being co-located within a single processing unit, in implementations in which processor 110 includes multiple processing units, one or more of components 111-113 may be located remotely from the other components. The description of the functionality provided by the different components 111-113 described below is for illustrative purposes, and is not intended to be limiting, as any of components 111-113 may provide more or less functionality than is described. For example, one or more of components 111-113 may be eliminated, and some or all of its functionality may be provided by other ones of components 111-113. Note that processor 110 may be configured to execute one or more additional components that may perform some or all of the functionality attributed below to one of components 111-113.

Parameter determination component 111 of system 5 in FIG. 2A is configured to determine one or more gas parameters, respiratory parameters, medical parameters, environmental parameters, and/or other parameters from output signals generated by one or more sensors 142. The one or more gas parameter may include and/or be related to one or more of (peak) flow, flow rate, (tidal) volume, pressure, temperature, humidity, velocity, acceleration, gas composition (e.g. concentration(s) of one or more constituents such as, e.g., $CO_2$), thermal energy dissipated, (intentional) gas leak, and/or other measurements related to the (pressurized) flow of breathable gas. One or more breathing parameters may be derived from gas parameters and/or other output signals conveying measurements of the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters. Some or all of this functionality may be incorporated, shared, and/or integrated into other computer program components of processor 110.

Environmental parameters may be related to one or more of the parameters of electromagnetic radiation, various temperatures, humidity level, and/or other environmental parameters, which may be related to environmental conditions near system 5 or near subject 106. One or more medical parameters may be related to monitored vital signs of subject 106, physiological parameters of subject 106, and/or other medical parameters of subject 106. Some or all of this functionality can be incorporated or integrated into other computer program components of processor 110.

Timing component 112 of system 5 in FIG. 2A is configured to determine one or more timing parameters related to the respiration of subject 106. In some embodiments, timing component 112 is configured to determine whether a current respiratory phase is an inhalation phase or an exhalation phase. In some embodiments, timing component 112 may be configured to determine respiratory timing parameters and/or other timing parameters related to the operation of system 100, such as transitions in breathing between inhalations and exhalations. Respiratory timing parameters may include transitional moments that separate inhalation phases from exhalation phases and/or vice versa, breathing period, respiratory rate, inhalation time or period, exhalation time or period, start and/or end of inhalation phases, start and/or end of exhalation phases, and/or other respiratory timing parameters. One or more determinations by timing component 112 may be used, shared, and/or incorporated in other components of system 100.

Control component 113 is configured to control operation of system 5, apparatus 10, and/or pressure generator 140 (or components thereof) in multiple modes of operation. For example, control component 113 may be configured to adjust and/or control opening and closing (and/or the degree of opening and closing) of valve 15, in particular during exhalation of subject 106 in order to regulate exhaust through valve 15. For example, control component 113 may be configured to adjust and/or control first control port 12, second control port 16, and/or other components of apparatus 10. Control component 113 may be configured to control transitions between different modes of operation. Control component 113 may be configured to determine what the current mode of operation is, and/or share such information with other components of system 5. Control component 113 may be configured to control pressure generator 140 such that one or more gas parameters of the pressurized flow of breathable gas are varied over time in accordance with a respiratory therapy regimen. Control component 113 may be configured to control pressure generator 140 to provide the pressurized flow of breathable gas at inhalation pressure levels during inhalation phases, and at exhalation pressure levels during exhalation phases. Parameters determined by parameter determination component 111, timing component 112, and/or received through sensors 142 may be used by control component 113, e.g. in a feedback manner, to adjust one or more therapy modes/settings/operations of system 5. Alternatively, and/or simultaneously, signals and/or information received through user interface 120 may be used by control component 113, e.g. in a feedback manner, to adjust one or more therapy modes/settings/operations of system 5. Control component 111 may be configured to time its operations relative to the transitional moments in the breathing cycle of a subject, over multiple breath cycles, and/or in any other relation to any detected occurrences or determinations by timing component 112.

Figure 3:
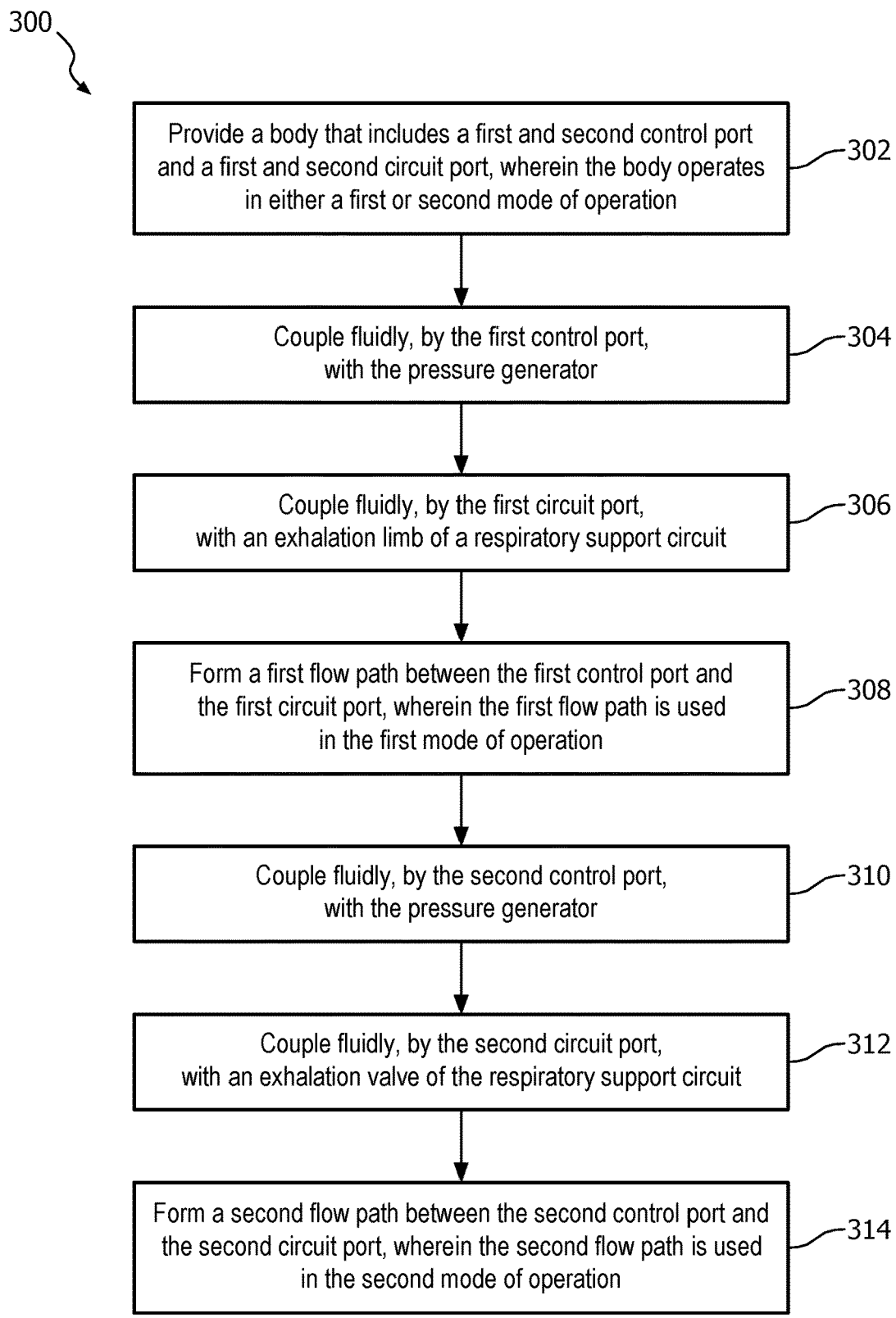
FIG. 3 illustrates a method for coupling a respiratory support circuit to a pressure generator in accordance with one or more embodiments.

FIG. 3 illustrates a method 300 for coupling a respiratory support circuit to a pressure generator. The operations of method 300 presented below are intended to be illustrative. In some embodiments, method 300 is accomplished with one or more additional operations not described, and/or without one or more of the operations discussed. Additionally, the order in which the operations of method 300 are illustrated in FIG. 3 and described below is not intended to be limiting.

In some embodiments, method 300 is implemented in one or more processing devices (e.g., a digital processor, a microcontroller, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 500.

At an operation 302, a body is provided that includes a first and second control port and a first and second circuit port. The body operates in either a first mode or a second mode of operation. In some embodiments, operation 302 is performed by a body the same as or similar to body 11 (shown in FIG. 1 and described herein).

At an operation 304, a control port couples fluidly with the pressure generator. In some embodiments, operation 304 is performed by a control port the same as or similar to first control port 12 (shown in FIG. 1 and described herein).

At an operation 306, a circuit port couples fluidly with an exhalation limb of the respiratory support circuit. In some embodiments, operation 306 is performed by a circuit port the same as or similar to first circuit port 14 (shown in FIG. 1 and described herein).

At an operation 308, a first flow path is formed between a control port and a circuit port. The first flow path is used in the first mode of operation. In some embodiments, operation 308 is performed by a first flow path the same as or similar to first flow path 13 (shown in FIG. 1 and described herein).

At an operation 310, a control port couples fluidly with the pressure generator. In some embodiments, operation 310 is performed by a control port the same as or similar to second control port 16 (shown in FIG. 1 and described herein).

At an operation 312, a circuit port couples fluidly with an exhalation valve of the respiratory support circuit. In some embodiments, operation 312 is performed by a circuit port the same as or similar to second circuit port 18 (shown in FIG. 1 and described herein).

At an operation 314, a second flow path is formed between a control port and a circuit port. The second flow path is used in the second mode of operation. In some embodiments, operation 314 is performed by a second flow path the same as or similar to second flow path 17 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An apparatus comprising:
a body configured to be coupled operatively with a pressure generator and tubing to provide a respiratory support circuit to a subject, wherein the body is configured to effectuate switching between a first mode of operation and a second mode of operation, the body comprising:
a first control port configured to couple fluidly with the pressure generator;
a first circuit port configured to couple fluidly with an exhalation limb of the respiratory support circuit;
a first flow path formed between the first control port and the first circuit port, wherein the first flow path is used in the first mode of operation;
a second control port different than the first control port, the second control port configured to couple fluidly with the pressure generator;
a second circuit port configured to couple fluidly with an exhalation valve of the respiratory support circuit; and
a second flow path formed between the second control port and the second circuit port, wherein the second flow path is used in the second mode of operation,
wherein the body is configured to move relative to the pressure generator to switch between the first mode of operation and the second mode of operation, wherein the body is configured to be in a first position relative to the pressure generator responsive to the respiratory support circuit operating in the first mode of operation, and wherein the body is configured to move to a second position relative to the pressure generator responsive to the respiratory support circuit operating in the second mode of operation, the second position being different than the first position,
wherein the body comprises a symmetry axis, wherein the body is configured to move about the symmetry axis to switch between the first mode of operation and the second mode of operation, wherein the body is configured to move about the symmetry axis from the first position to the second position relative to the pressure generator responsive to the respiratory support circuit being switched from operating in the first mode of operation to operating in the second mode of operation.

2. The system of claim 1, further comprising a valve, arranged within the first flow path, configured to selectively exhaust gas from the exhalation limb of the respiratory support circuit.

3. The system of claim 1, wherein the first control port is configured to couple fluidly with the pressure generator at a location of the pressure generator, and wherein the second control port is configured to couple fluidly with the pressure generator at the same location of the pressure generator.

4. The system of claim 1, wherein the respiratory support circuit includes a dual-limb configuration in the first mode of operation, and wherein the respiratory support circuit includes a proximal airway pressure in the second mode of operation.

5. The system of claim 1, wherein switching between the first mode of operation and the second mode of operation is effectuated by switching the position of the body relative to the pressure generator between the first position and the second position.

6. A method of coupling a respiratory support circuit to a pressure generator, the method comprising:
providing a body that includes a first and second control port and a first and second circuit port, the second control port being different than the first control port, and a symmetry axis, wherein the body operates in either a first mode or a second mode of operation;
coupling fluidly, by the first control port, with the pressure generator;
coupling fluidly, by the first circuit port, with an exhalation limb of the respiratory support circuit;
forming a first flow path between the first control port and the first circuit port, wherein the first flow path is used in the first mode of operation;
coupling fluidly, by the second control port, with the pressure generator;
coupling fluidly, by the second circuit port, with an exhalation valve of the respiratory support circuit;
forming a second flow path between the second control port and the second circuit port, wherein the second flow path is used in the second mode of operation,
moving the body relative to the pressure generator to switch between the first mode of operation and the second mode of operation, wherein the body is configured to be in a first position relative to the pressure generator responsive to the respiratory support circuit operating in the first mode of operation, and wherein the body is configured to move to a second position relative to the pressure generator responsive to the respiratory support circuit operating in the second mode of operation, the second position being different than the first position; and
moving the body about the symmetry axis to switch between the first mode of operation and the second mode of operation, wherein the body is configured to move about the symmetry axis from the first position to the second position relative to the pressure generator responsive to the respiratory support circuit being switched from operating in the first mode of operation to operating in the second mode of operation.

7. The method of claim 6, further comprising selectively exhausting, by a valve arranged within the first flow path, gas from the exhalation limb of the respiratory support circuit.

8. The method of claim 6, wherein coupling fluidly, by the first control port, with the pressure generator includes coupling fluidly with the pressure generator at a location of the pressure generator, and coupling fluidly, by the second control port, with the pressure generator includes coupling fluidly with the pressure generator at the same location of the pressure generator.

9. The method of claim 6, further comprising at least one of:
operating, in the first mode of operation, the respiratory support circuit by using a dual-limb configuration; and
operating, in the second mode of operation, the respiratory support circuit by using proximal airway pressure.

10. The method of claim 6, further comprising switching between the first mode of operation and the second mode of operation is effectuated by switching the position of the body relative to the pressure generator between the first position and the second position.

11. A system configured to couple a respiratory support circuit to a pressure generator, the system comprising:
means for switching between a first mode and a second mode of operation, the means for switching comprising:
first means for coupling fluidly with the pressure generator;
means for coupling fluidly with an exhalation limb of the respiratory support circuit;
means for forming a first flow path between the first control port and the first circuit port, the means for forming the first flow path being used in the first mode of operation;
second means for coupling fluidly with the pressure generator, the second means for coupling being different than the first means for coupling;
means for coupling fluidly with an exhalation valve of the respiratory support circuit; and
means for forming a second flow path between the second control port and the second circuit port, the means for forming the second flow path being used in the second mode of operation, wherein the means for switching between a first mode and a second mode of operation is configured to move relative to the pressure generator to switch between the first mode of operation and the second mode of operation, wherein the means for switching is configured to be in a first position relative to the pressure generator responsive to the respiratory support circuit operating in the first mode of operation, and wherein the means for switching is configured to move to a second position relative to the pressure generator responsive to the respiratory support circuit operating in the second mode of operation, the second position being different than the first position, wherein the means for switching between a first mode and a second mode of operation comprises a symmetry axis, wherein the means for switching between a first mode and a second mode of operation is configured to move about the symmetry axis to switch between the first mode of operation and the second mode of operation, wherein the means for switching is configured to move about the symmetry axis from the first position to the second position relative to the pressure generator responsive to the respiratory support circuit being switched from operating in the first mode of operation to operating in the second mode of operation.

12. The system of claim 11, further comprising means for selectively exhausting gas from the exhalation limb of the respiratory support circuit.

13. The system of claim 11, wherein the first means for coupling fluidly with the pressure generator is configured to couple fluidly with the pressure generator at a location of the pressure generator, and wherein the second means for coupling fluidly with the pressure generator is configured to couple fluidly with the pressure generator at the same location of the pressure generator.

14. The system of claim 11, wherein, responsive to the respiratory support circuit operating in the first mode of operation, the respiratory support circuit operates by using a dual-limb configuration; and wherein, responsive to the respiratory support circuit operating in the second mode of operation, the respiratory support circuit operates by using proximal airway pressure.

15. The system of claim 11, wherein switching between the first mode of operation and the second mode of operation is effectuated by switching the position of the means for switching between the first position and the second position relative to the pressure generator.

* * * * *